(12) United States Patent
Diehn et al.

(10) Patent No.: US 7,214,854 B2
(45) Date of Patent: May 8, 2007

(54) MAIZE METALLOTHIONEIN PROMOTER

(75) Inventors: Scott Diehn, West Des Moines, IA (US); Albert L. Lu, Newark, DE (US)

(73) Assignees: Pioneer Hi-Bred International, Inc., Johnston, IA (US); E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/022,111

(22) Filed: Dec. 22, 2004

(65) Prior Publication Data

US 2005/0177897 A1 Aug. 11, 2005

Related U.S. Application Data

(60) Provisional application No. 60/531,793, filed on Dec. 22, 2003, provisional application No. 60/532,180, filed on Dec. 23, 2003.

(51) Int. Cl.
*C12N 15/82* (2006.01)
*A01H 5/00* (2006.01)
*C07H 21/04* (2006.01)

(52) U.S. Cl. ............ 800/287; 800/278; 435/468; 435/419; 435/320.1; 536/24.1

(58) Field of Classification Search .......... None
See application file for complete search history.

(56) References Cited

U.S. PATENT DOCUMENTS

| 5,466,785 | A | 11/1995 | De Framond |
| 6,774,282 | B1 | 8/2004 | Ritchie |
| 2002/0100079 | A1 | 7/2002 | Bruce |
| 2002/0132139 | A1 | 10/2002 | Bruce |
| 2004/0123345 | A1 | 6/2004 | Bruce |
| 2005/0010974 | A1 | 1/2005 | Milligan et al. |
| 2005/0177898 | A1* | 8/2005 | Diehn et al. ............ 800/278 |
| 2006/0005274 | A1* | 1/2006 | Diehn et al. ............ 800/279 |

FOREIGN PATENT DOCUMENTS

| EP | 0 452 269 A2 | | 10/1991 |
| WO | WO 00/53763 | * | 9/2000 |
| WO | WO 03/040322 A2 | | 5/2003 |

OTHER PUBLICATIONS

Kim et al. A 20 nucleotide upstream element is essential for the nopaline synthase (nos) promoter activity. (1994) PMB, vol. 24, pp. 105-117.*
Kawashima, I., et al., "Wheat $E_c$ Metallothionein Genes/ Like Mammalian $Zn^{2+}$ Metallothionein Genes, Wheat $Zn^{2+}$ Metallothionein Genes are Conspicuously Expressed During Embryogenesis," *Eur. J. Biochem*, 1992, pp. 971-976, vol. 209.
Thomas, J.C., et al., "Yeast Metallothionein in Transgenic Tobacco Promotes Copper Uptake from Contaminated Soils," *Biotechnol. Prog.*, 2003, pp. 273-280, vol. 19.
Ahmadi, N., et al. "The Promoter of Metallothionein-like Gene from the Tropical Tree *Casuarina glauca* is Active in both Annual Dicotyledonous and Monotyledonous Plants," *Transgenic Research*, 2003, pp. 271-281, vol. 12.
Charbonnel-Campa, L., et al. "Isolation of a Type 2 Metallothionein-like Gene Preferentially Expressed in the Tapetum in *Zea mays*," *Gene*, 2000, pp. 199-208, vol. 254, No. 1-2.
De Framond, A. J., "A Metallothionein-like Gene from Maize (*Zea mays*) Cloning and Characterization," *FEBS Letters*, 1991, pp. 103-106, vol. 290, No. 1-2.
Hudspeth, R. L., et al. "Characterization and Expression of Metallothionein-like Genes in Cotton," *Plant Molecular Biology*, 1996, pp. 701-705, vol. 31.
White, C. N. and Rivin, C. J., "Characterization and Expression of a cDNA Encoding a Seed-Specific Metallothionein in Maize," *Plant Physiol.*, 1995, pp. 931-832, vol. 108.
Zhou, J. and Goldsbrough, P. B., "Structure, Organization and Expression of the Metallothionein Gene Family in *Arabidosis*," *Mol Gen Genet*, 1995, pp. 318-328, vol. 248.
Hsieh, H.-M. and P.C. Huang, Promoter Structure and Activity of Type 1 Rice Methallothionein-Like Gene, *The Journal of Sequencing and Mapping*, 1998, pp. 9-18, vol. 9(1).
Hsieh, H.-M., et al. "A Novel Stress-Inducible Metallothionein-Like Gene From Rice," *Plant Molecular Biology*, 1995, pp. 381-389, vol. 28.
Benfey, et al., The Cauliflower Mosaic Virus 35S Promoter: Cominatorial Regulation of Transcription in Plants, *Science*, 1990, pp. 959-966, vol. 250.
Doelling, et al., "The Minimal Ribosomal RNA Gene Promoter of *Arabidopsis thaliana* Includes a Critical Element at the Transcription Initiation Site." *The Plant Journal*, 1995, pp. 683-692, vol. 8.
Maiti, et al., "Promoter/Leader-Deletion Analysis and Plant Expression Vectors with the Figwort Mosaic Virus (FMV) Full Length Transcript (FLt) Promoter Containing Single or Double Enhancer Domains," *Transgenic Research*, 1997, pp. 143-156, vol. 6.

* cited by examiner

*Primary Examiner*—Anne Kubelik
*Assistant Examiner*—Cathy Kingdon Worley
(74) *Attorney, Agent, or Firm*—Alston & Bird LLP

(57) ABSTRACT

The present invention provides compositions and methods for regulating expression of heterologous nucleotide sequences in a plant. Compositions include a novel nucleotide sequence for a maize metallothionein promoter for the gene encoding metallothionein. A method for expressing a heterologous nucleotide sequence in a plant using the promoter sequences disclosed herein is provided. The method comprises transforming a plant or plant cell with a nucleotide sequence operably linked to one of the promoters of the present invention.

20 Claims, No Drawings

SEQUENCE LISTING

<160> NUMBER OF SEQ ID NOS: 16

<210> SEQ ID NO 1
<211> LENGTH: 1815
<212> TYPE: DNA
<213> ORGANISM: Zea mays
<220> FEATURE:
<221> NAME/KEY: promoter
<222> LOCATION: (1)...(1815)
<223> OTHER INFORMATION: Metallothionein Promoter

<400> SEQUENCE: 1

```
tgactcatgt gtggtatgta aagaaacaag ttatgctcaa gaaagccgtt aagcagtgac      60
cttctccctc agctttccct tctttgcttg cacttcttgg ttgtttggtc cttcataaac     120
aagcattcaa caggcagaga ttaaactacc tgcctaatgg ctaaatgggc acgtataaac     180
caaggaggta cctgaaggct gagaggtaga ctgctcatcc gacagttctg ttgccacgat     240
ctttgccctc cggtcgacga cttcgagcaa gtctattaca aaaaggaaca acatgctcag     300
attccatatt gcaaactcat cacagtgcaa tcaagcaggc agaaacggtg atgggtttca     360
gttatgtgcg attaggccgc agaatgacca aacagagtac acagccacag ctgtaggaaa     420
tactagaatc acggagtaat caacgcgcgg aaactacaag ggttgtggga tggtgggaac     480
tggggaggac ggcagatctt cgctggcgaa gagaggtgga tctgtgtggc gcgccaagat     540
agggcgaggg aggtcgggcc gtcaggaggc cgtaccttcg gcgaccttga gccatgaggc     600
catggcggaa tccccgctgg tagcgcggtg tgacggcgag tgagcttgat gaattgggtg     660
gtgtgagatc tccggccacg gcagtgtgct tcgaagtaag ctgtcgcaga ctcgcagctc     720
gcaatggtgg gtgccggtgc ggggcgaaag gttgcacatt tgtttagata caatactaag     780
cagttttttg tatcttcgcc cgtctagctc agttggtaga gcgcaaagct cttaaccttg     840
tggtcgtggg ttcgagcccc acggtgggcg cacaattttt tgttttttga catttttttgt     900 ttgcttagtt gcagacggtt tttcccctgc taggagattt ccgagagaaa aaaaggcac     960 tacaggttaa ccaaaaccac caacctttgg agcgtcgagg cgacgggcat ttgcgtagtt    1020
gaagcttaca aagttgcata tgagatgagt gccggacatg aagcggataa cgtttttaaac    1080 tggcaacaat atctagctgt ttcaaattca ggcgtgggaa gctacgccta cgcgccctgg    1140
acggcgtgta aagagccagc atcggcatca ttgtcaaacg atcgacaagg ccaagaaatt    1200
ccaaatatat tattaataaa aagaaggca caaattagtt tggttttta gtatgtgtgg    1260 cggaggaaat tttgagaacg aacgtatcaa agaaggcaca agacgatata gattgacgcg    1320
gctagaagtt gcagcaagac agtgggtacg gtcttatata tcctaataaa taaaaaataa    1380
aactatagtg tgtcaaatgt caacaagagg aggaggcagc caaattagca gagggagaca    1440
agtagagcac gccttattag cttgcttatt tatcgtggtg gtgtacttgt taattactgg    1500
```

| | |
|---|---|
| cacgcattat caacaacgca gttctggatg tgaatctaga caaacatttg tctaggttcc | 1560 |
| gcacgtatag ttttttttcct cttttttttg ggggggggt ggggggggga acggaagctg | 1620 |
| taataaacgg tactaggaac gaaagcaacc gccgcgcgca tgttttttgca atagattacg | 1680 |
| gtgaccttga tgcaccaccg cgtgctataa aaaccagtgt ccccgagtct actcatcaac | 1740 |
| caatccataa ctcgaaacct tttcttgtgc tctgttctgt ctgtgtgttt ccaaagcaag | 1800 |
| cgaaagaggt cgagg | 1815 |

<210> SEQ ID NO 2
<211> LENGTH: 747
<212> TYPE: DNA
<213> ORGANISM: Zea mays
<220> FEATURE:
<221> NAME/KEY: promoter
<222> LOCATION: (1)...(747)
<223> OTHER INFORMATION: Metallothionein promoter

<400> SEQUENCE: 2

| | |
|---|---|
| cgacgggcat ttgcgtagtt gaagcttaca aagttgcata tgagatgagt gccggacatg | 60 |
| aagcggataa cgttttaaac tggcaacaat atctagctgt ttcaaattca ggcgtgggaa | 120 |
| gctacgccta cgcgccctgg acggcgtgta aagagccagc atcggcatca ttgtcaaacg | 180 |
| atcgacaagg ccaagaaatt ccaaatatat tattaataaa aagaaggca caaattagtt | 240 |
| tggttttta gtatgtgtgg cggaggaaat tttgagaacg aacgtatcaa agaaggcaca | 300 |
| agacgatata gattgacgcg gctagaagtt gcagcaagac agtgggtacg gtcttatata | 360 |
| tcctaataaa taaaaaataa aactatagtg tgtcaaatgt caacaagagg aggaggcagc | 420 |
| caaattagca gagggagaca agtagagcac gccttattag cttgcttatt tatcgtggtg | 480 |
| gtgtacttgt taattactgg cacgcattat caacaacgca gttctggatg tgaatctaga | 540 |
| caaacatttg tctaggttcc gcacgtatag ttttttttcct cttttttttg ggggggggt | 600 |
| ggggggggga acggaagctg taataaacgg tactaggaac gaaagcaacc gccgcgcgca | 660 |
| tgttttttgca atagattacg gtgaccttga tgcaccaccg cgtgctataa aaaccagtgt | 720 |
| ccccgagtct actcatcaac caatcca | 747 |

<210> SEQ ID NO 3
<211> LENGTH: 27
<212> TYPE: DNA
<213> ORGANISM: Artificial Sequence
<220> FEATURE:
<223> OTHER INFORMATION: Primer named rootmet5

<400> SEQUENCE: 3

| | |
|---|---|
| ccgtggggct cgaacccacg accacaa | 27 |

<210> SEQ ID NO 4
<211> LENGTH: 27
<212> TYPE: DNA
<213> ORGANISM: Artificial Sequence
<220> FEATURE:
<223> OTHER INFORMATION: Primer named rootmet7

<400> SEQUENCE: 4

| | |
|---|---|
| cgactgagct agacgggcct cttgtaa | 27 |

<210> SEQ ID NO 5
<211> LENGTH: 30
<212> TYPE: DNA

-continued

<213> ORGANISM: Artificial Sequence
<220> FEATURE:
<223> OTHER INFORMATION: Primer named rootmet1

<400> SEQUENCE: 5
tgatgccgat gctggctctt tacacgccgt                                30

<210> SEQ ID NO 6
<211> LENGTH: 30
<212> TYPE: DNA
<213> ORGANISM: Artificial Sequence
<220> FEATURE:
<223> OTHER INFORMATION: Primer named rootmet2

<400> SEQUENCE: 6
cagctagata ttgttgccac tttaaaacgt                                30

<210> SEQ ID NO 7
<211> LENGTH: 36
<212> TYPE: DNA
<213> ORGANISM: Artificial Sequence
<220> FEATURE:
<223> OTHER INFORMATION: Primer named rootmet3KRW3

<400> SEQUENCE: 7
tcacaccgcg ctaccagcgg ggattccgcc atggcc                         36

<210> SEQ ID NO 8
<211> LENGTH: 36
<212> TYPE: DNA
<213> ORGANISM: Artificial Sequence
<220> FEATURE:
<223> OTHER INFORMATION: Primer named rootmet3KRW4

<400> SEQUENCE: 8
gcctcatggc tcaaggtcgc cgaaggtacg gcctcc                         36

<210> SEQ ID NO 9
<211> LENGTH: 39
<212> TYPE: DNA
<213> ORGANISM: Artificial Sequence
<220> FEATURE:
<223> OTHER INFORMATION: Primer named RMSOE1

<400> SEQUENCE: 9
ggatcctgac tcatgtgtgg tatgtaaaga aacaagtta                      39

<210> SEQ ID NO 10
<211> LENGTH: 42
<212> TYPE: DNA
<213> ORGANISM: Artificial Sequence
<220> FEATURE:
<223> OTHER INFORMATION: Primer named RMSOE4

<400> SEQUENCE: 10
aaaacaaaaa attgtgcgcc caccgtgggg ctcgaaccca cg                  42

<210> SEQ ID NO 11
<211> LENGTH: 42
<212> TYPE: DNA
<213> ORGANISM: Artificial Sequence
<220> FEATURE:
<223> OTHER INFORMATION: Primer named RMSOE3

<400> SEQUENCE: 11
tgtggtcgtg ggttcgagcc ccacggtggg cgcacaattt tt                  42

```
<210> SEQ ID NO 12
<211> LENGTH: 42
<212> TYPE: DNA
<213> ORGANISM: Artificial Sequence
<220> FEATURE:
<223> OTHER INFORMATION: Primer named RMSOE2

<400> SEQUENCE: 12
ttgttgataa tgcgtgccag taattaacaa gtacaccacc ac                          42

<210> SEQ ID NO 13
<211> LENGTH: 33
<212> TYPE: DNA
<213> ORGANISM: Artificial Sequence
<220> FEATURE:
<223> OTHER INFORMATION: Primer named BAMrootmetpro8

<400> SEQUENCE: 13
ggatcctgac tcatgtgtgg tatgtaaaga aac                                    33

<210> SEQ ID NO 14
<211> LENGTH: 33
<212> TYPE: DNA
<213> ORGANISM: Artificial Sequence
<220> FEATURE:
<223> OTHER INFORMATION: Primer named pSOEB

<400> SEQUENCE: 14
tcgatcgttt gacaatgatg ccgatgctgg ctc                                    33

<210> SEQ ID NO 15
<211> LENGTH: 33
<212> TYPE: DNA
<213> ORGANISM: Artificial Sequence
<220> FEATURE:
<223> OTHER INFORMATION: Primer named pSOEA

<400> SEQUENCE: 15
catcattgtc aaacgatcga caaggccaag aaa                                    33

<210> SEQ ID NO 16
<211> LENGTH: 33
<212> TYPE: DNA
<213> ORGANISM: Artificial Sequence
<220> FEATURE:
<223> OTHER INFORMATION: Primer named Xhorootmet1b

<400> SEQUENCE: 16
ctcgagcctc gacctctttc gcttgctttg gaa                                    33
```

MAIZE METALLOTHIONEIN PROMOTER

CROSS REFERENCE TO RELATED APPLICATIONS

This application claims priority to U.S. Provisional Application No. 60/531,793 filed on Dec. 22, 2003 and U.S. Provisional Application No. 60/532,180 filed on Dec. 23, 2003, both of which are herein incorporated by reference in its entirety.

FIELD OF THE INVENTION

The present invention relates to the field of plant molecular biology, more particularly to regulation of gene expression in plants.

BACKGROUND OF THE INVENTION

Expression of heterologous DNA sequences in a plant host is dependent upon the presence of an operably linked promoter that is functional within the plant host. Choice of the promoter sequence will determine when and where within the organism the heterologous DNA sequence is expressed. Where expression in specific tissues or organs is desired, tissue-preferred promoters may be used. Where gene expression in response to a stimulus is desired, inducible promoters are the regulatory element of choice. In contrast, where continuous expression is desired throughout the cells of a plant, constitutive promoters are utilized. Additional regulatory sequences upstream and/or downstream from the core promoter sequence may be included in the expression constructs of transformation vectors to bring about varying levels of expression of heterologous nucleotide sequences in a transgenic plant.

Frequently it is desirable to express a DNA sequence in particular tissues or organs of a plant. For example, increased resistance of a plant to infection by soil- and air-borne pathogens might be accomplished by genetic manipulation of the plant's genome to comprise a tissue-preferred promoter operably linked to a heterologous pathogen-resistance gene such that pathogen-resistance proteins are produced in the desired plant tissue.

Alternatively, it might be desirable to inhibit expression of a native DNA sequence within a plant's tissues to achieve a desired phenotype. In this case, such inhibition might be accomplished with transformation of the plant to comprise a tissue-preferred promoter operably linked to an antisense nucleotide sequence, such that expression of the antisense sequence produces an RNA transcript that interferes with translation of the mRNA of the native DNA sequence.

Thus far, the regulation of gene expression in plant roots has not been adequately studied despite the importance of the root to plant development. To some degree this is attributable to a lack of readily available, root-specific biochemical functions whose genes may be cloned, studied, and manipulated. Genetically altering plants through the use of genetic engineering techniques and thus producing a plant with useful traits requires the availability of a variety of promoters. An accumulation of promoters would enable the investigator to design recombinant DNA molecules that are capable of being expressed at desired levels and cellular locales. Therefore, a collection of tissue-preferred promoters would allow for a new trait to be expressed in the desired tissue. Several genes have been described by Takahashi et al. (1991) *Plant J.* 1:327–332; Takahashi et al. (1990) *Proc. Natl. Acad. Sci. USA* 87:8013–8016; Hertig et al. (1991) *Plant Mol Biol.* 16:171–174; Xu et al. (1995) *Plant Mol Biol.* 27:237–248; Capone et al. (1994) *Plant Mol Biol.* 25:681–691; Masuda et al. (1999) *Plant Cell Physiol.* 40(11):1177–81; Luschnig et al. (1998) *Genes Dev.* 12(14): 2175–87; Goddemeier et al. (1998) *Plant Mol Biol.* 36(5): 799–802; and Yamamoto et al. (1991) *Plant Cell.* 3(4): 371–82 to express preferentially in plant root tissues.

Metallothioneins (MT's) are proteins or polypeptides that bind and sequester ionic forms of certain metals in plant and animal tissues. Examples of such metals include copper, zinc, cadmium, mercury, gold, silver, cobalt, nickel and bismuth. The specific metals sequestered by MT's vary for the structurally distinct proteins/polypeptides occurring in different organisms. Plants appear to contain a diversity of metal-binding MT's with the potential to perform distinct roles in the metabolism of different metal ions. In plants, MT's are suggested to have roles in metal accumulation, metal intoxication, and embryogenesis (Thomas et al. (2003) *Biotechnol. Prog.* 19:273–280; Dong and Dunstan (1996) *Planta* 199:459–466; Kawashima et al. (1992) *Eur. J. Biochem.* 209:971–976).

Typically, MT's and MT-like proteins are Cys-rich proteins that are characterized by the presence of Cys-Xaa-Cys motifs suggesting the capability of binding metal ions. Further categories of MT-like proteins have been proposed on the basis of the predicted locations of Cys residues and have been designated types 1 and 2. In type 1 there are exclusively Cys-Xaa-Cys motifs, whereas in type 2 there is a Cys-Cys and a Cys-Xaa-Xaa-Cys pair within the N-terminal domain. The type 1 motif has been implicated in the binding and sequestration of copper (Murphy et al. (1997) *Plant Physiol.* 113:1293–1301 and Carr et al. (2002) *J. Biol. Chem.* 277:31237–31242).

Several metallothionein-like plant genes have been isolated, including those from pea, maize, barley, *Mimulus* (monkeyflower), soybean, castor bean and *Arabidopsis*. See Robinson et al. (1993) *Biochem J.* 295: 1–10. Sequences expressed in roots have been reported to be isolated from pea, as described in Evans et al. (1990) *FEBS Lett* 262: 29–32. A maize root MT gene has been described in U.S. Pat. No. 5,466,785; though this sequence is also expressed in leaves, pith and seed, as described in de Framond (1991) *FEBS Lett* 290:103–106.

Thus, isolation and characterization of tissue-preferred, particularly root-preferred, promoters that can serve as regulatory regions for expression of heterologous nucleotide sequences of interest in a tissue-preferred manner are needed for genetic manipulation of plants.

SUMMARY OF THE INVENTION

Compositions and methods for regulating expression of a heterologous nucleotide sequence of interest in a plant or plant cell are provided. Compositions comprise novel nucleotide sequences for promoters that initiate transcription. Embodiments of the invention comprise the nucleotide sequence set forth in SEQ ID NO: 1 or a complement thereof, the nucleotide sequence comprising the plant promoter sequence of the plasmid deposited as Patent Deposit No. NRRL B-30792 or a complement thereof; a nucleotide sequence comprising at least 20 contiguous nucleotides of SEQ ID NO: 1, wherein said sequence initiates transcription in a plant cell; and, a nucleotide sequence comprising a sequence having at least 85% sequence identity to the sequence set forth in SEQ ID NO:1, wherein said sequence initiates transcription in the plant cell.

A method for expressing a heterologous nucleotide sequence in a plant or plant cell is provided. The method comprises introducing into a plant or a plant cell an expression cassette comprising a heterologous nucleotide sequence interest operably linked to one of the promoters of the present invention. In this manner, the promoter sequences are useful for controlling the expression of the operably linked heterologous nucleotide sequence. In specific methods, the heterologous nucleotide sequence of interest is expressed in a root-preferred manner.

Further provided is a method for expressing a nucleotide sequence of interest in a root-preferred manner in a plant. The method comprises introducing into a plant cell an expression cassette comprising a promoter of the invention operably linked to a heterologous nucleotide sequence of interest.

Expression of the nucleotide sequence of interest can provide for modification of the phenotype of the plant. Such modification includes modulating the production of an endogenous product, as to amount, relative distribution, or the like, or production of an exogenous expression product to provide for a novel function or product in the plant. In specific methods and compositions, the heterologous nucleotide sequence of interest comprises a gene product that confers herbicide resistance, pathogen resistance, insect resistance, and/or altered tolerance to salt, cold, or drought.

Expression cassettes comprising the promoter sequences of the invention operably linked to a heterologous nucleotide sequence of interest are provided. Additionally provided are transformed plant cells, plant tissues, seeds, and plants.

DETAILED DESCRIPTION OF THE INVENTION

The invention relates to compositions and methods drawn to plant promoters and methods of their use. The compositions comprise nucleotide sequences for the promoter region of the metallothionein (MT) gene. The compositions further comprise DNA constructs comprising a nucleotide sequence for the promoter region of the metallothionein 1 (MT1) gene operably linked to a heterologous nucleotide sequence of interest. In particular, the present invention provides for isolated nucleic acid molecules comprising the nucleotide sequence set forth in SEQ ID NO: 1, and the plant promoter sequence deposited in bacterial hosts as Patent Deposit No. NRRL B-30792, on Dec. 1, 2004, and fragments, variants, and complements thereof.

Plasmids containing the plant promoter nucleotide sequences of the invention were deposited on Dec. 1, 2004 with the Patent Depository of the Agricultural Research Service Culture Collection of the National Center for Agricultural Utilization Research, at 1815 N. University Street, Peoria, Ill., 61604, and assigned Patent Deposit No. NRRL B-30792. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112. The deposit will irrevocably and without restriction or condition be available to the public upon issuance of a patent. However, it should be understood that the availability of a deposit does not constitute a license to practice the subject invention in derogation of patent rights granted by government action.

The MT1 promoter sequences of the present invention include nucleotide constructs that allow initiation of transcription in a plant. In specific embodiments, the MT1 promoter sequence allows initiation of transcription in a tissue-preferred, more particularly in a root-preferred manner. Such constructs of the invention comprise regulated transcription initiation regions associated with plant developmental regulation. Thus, the compositions of the present invention comprise novel plant promoter nucleotide sequences, particularly root-preferred promoter sequences for the MT gene, more particularly a maize MT1 promoter sequence. The sequence for the maize MT1 promoter region is set forth in SEQ ID NO:1.

Compositions of the invention include the nucleotide sequences for the native MT1 promoter and fragments and variants thereof. The promoter sequences of the invention are useful for expressing sequences. In specific embodiments, the promoter sequences of the invention are useful for expressing sequences of interest in a tissue-preferred, particularly a root-preferred manner. The sequences of the invention also find use in the construction of expression vectors for subsequent expression of a heterologous nucleotide sequence in a plant of interest or as probes for the isolation of other MT1-like promoters.

Related metallothionein promoter sequences are disclosed in U.S. application Ser. No. 09/520,268 and in U.S. Provisional Application No. 60/532,180 filed Dec. 23, 2003, the disclosures of which are herein incorporated by reference. In particular, the present invention provides for isolated DNA constructs comprising the promoter sequence set forth in SEQ ID NO:1 operably linked to a nucleotide sequence of interest.

The invention encompasses isolated or substantially purified nucleic acid compositions. An "isolated" or "purified" nucleic acid molecule or biologically active portion thereof, is substantially free of other cellular material, or culture medium when produced by recombinant techniques, or substantially free of chemical precursors or other chemicals when chemically synthesized. An "isolated" nucleic acid is free of sequences (optimally protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. The MT1 promoter sequences of the invention may be isolated from the 5' untranslated region flanking their respective transcription initiation sites.

Fragments and variants of the disclosed promoter sequences are also encompassed by the present invention. In particular, fragments and variants of the MT1 promoter sequence of SEQ ID NO: 1 may be used in the DNA constructs of the invention. As used herein, the term "fragment" means a portion of the nucleic acid sequence. Fragments of an MT1 promoter sequence may retain the biological activity of initiating transcription. Alternatively, fragments of a nucleotide sequence that is useful as hybridization probes may not necessarily retain biological activity. Fragments of a nucleotide sequence for the promoter region of the MT1 gene may range from at least about 20 nucleotides, about 50 nucleotides, about 100 nucleotides, and up to the full-length nucleotide sequence of the invention for the promoter region of the gene.

A biologically active portion of an MT1 promoter can be prepared by isolating a portion of the MT1 promoter sequence of the invention, and assessing the promoter activity of the fragment. Nucleic acid molecules that are fragments of an MT1 promoter nucleotide sequence comprise at least about 16, 50, 75, 100, 150, 200, 250, 300, 350, 400, 450, 500, 550, 600, 650, 700, 800, 900, 1000, 1100, 1200, 1300, 1400, 1500, 1600, 1700, 1800 nucleotides, or up to the number of nucleotides present in a full-length MT1 promoter sequence disclosed herein (for example, 1815 nucleotides for SEQ ID NO: 1).

As used herein, the term "variants" means substantially similar sequences. For nucleotide sequences, naturally occurring variants can be identified with the use of well-known molecular biology techniques, such as, for example, with polymerase chain reaction (PCR) and hybridization techniques as outlined herein.

For nucleotide sequences, a variant comprises a deletion and/or addition of one or more nucleotides at one or more internal sites within the native polynucleotide and/or a substitution of one or more nucleotides at one or more sites in the native polynucleotide. As used herein, a "native" nucleotide sequence comprises a naturally occurring nucleotide sequence. For nucleotide sequences, naturally occurring variants can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis. Generally, variants of a particular nucleotide sequence of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular nucleotide sequence as determined by sequence alignment programs and parameters described elsewhere herein. A biologically active variant of a nucleotide sequence of the invention may differ from that sequence by as few as 1–15 nucleic acid residues, as few as 1–10, such as 6–10, as few as 5, as few as 4, 3, 2, or even 1 nucleic acid residue.

Variant nucleotide sequences also encompass sequences derived from a mutagenic and recombinogenic procedure such as DNA shuffling. With such a procedure, one or more different MT1 nucleotide sequences for the promoter can be manipulated to create a new MT1 promoter. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech.* 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458.

The nucleotide sequences of the invention can be used to isolate corresponding sequences from other organisms, particularly other plants, more particularly other monocots. In this manner, methods such as PCR, hybridization, and the like can be used to identify such sequences based on their sequence homology to the sequences set forth herein. Sequences isolated based on their sequence identity to the entire MT1 sequences set forth herein or to fragments thereof are encompassed by the present invention.

In a PCR approach, oligonucleotide primers can be designed for use in PCR reactions to amplify corresponding DNA sequences from genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.), hereinafter Sambrook. See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments from a chosen organism. The hybridization probes may be labeled with a detectable group such as $^{32}P$, or any other detectable marker. Thus, for example, probes for hybridization can be made by labeling synthetic oligonucleotides based on the MT1 promoter sequences of the invention. Methods for preparation of probes for hybridization and for construction of genomic libraries are generally known in the art and are disclosed in Sambrook.

For example, the entire MT1 promoter sequence disclosed herein, or one or more portions thereof, may be used as a probe capable of specifically hybridizing to corresponding MT1 promoter sequences and messenger RNAs. To achieve specific hybridization under a variety of conditions, such probes include sequences that are unique among MT1 promoter sequences and are at least about 10 nucleotides in length or at least about 20 nucleotides in length. Such probes may be used to amplify corresponding MT1 promoter sequences from a chosen plant by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Cloning: A Laboratory Manual* ($2^{nd}$ ed, Cold Spring Harbor Laboratory Press, Plainview, N.Y.)

Hybridization of such sequences may be carried out under stringent conditions. The terms "stringent conditions" and "stringent hybridization conditions" are intended to mean conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length or less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a final wash in 0.1×SSC at 60 to 65° C. for a duration of at least 30 minutes. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the $T_m$ (thermal melting point) can be approximated from the equation of Meinkoth and Wahl (1984) *Anal. Biochem.* 138:267–284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology-Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See also Sambrook.

Thus, isolated sequences that have root-preferred promoter activity and which hybridize under stringent conditions to the MT1 promoter sequences disclosed herein, or to fragments thereof, are encompassed by the present invention.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11–17; the local alignment algorithm of Smith et al. (1981) *Adv. Appl. Math.* 2:482; the global alignment algorithm of Needleman and Wunsch (1970) *J. Mol. Biol.* 48:443–453; the search-for-local alignment method of Pearson and Lipman (1988) *Proc. Natl. Acad. Sci.* 85:2444–2448; the algorithm of Karlin and Altschul (1990) *Proc. Natl. Acad. Sci. USA* 872264, as modified in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *CABIOS* 8:155–65; and Pearson et al. (1994) *Meth. Mol. Biol.* 24:307–331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, and PSI-BLAST, the default parameters of the respective programs (e.g., BLASTN for nucleotide sequences, BLASTX for proteins) can be used. See the National Center for Biotechnology Information website on the world wide web at ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3 and the nwsgapdna.cmp scoring matrix; or any equivalent program thereof. By "equivalent program" is intended to mean any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters.

Another indication that nucleotide sequences are substantially identical is if two molecules hybridize to each other under stringent conditions. Generally, stringent conditions are selected to be about 5° C. lower than the $T_m$ for the specific sequence at a defined ionic strength and pH. However, stringent conditions encompass temperatures in the range of about 1° C. to about 20° C. lower than the $T_m$, depending upon the desired degree of stringency as otherwise qualified herein.

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotide.

The present invention may be used for transformation of any plant species, including, but not limited to, monocots and dicots. Examples of plant species include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Heterologous coding sequences expressed by the MT1 promoters of the invention may be used for varying the phenotype of a plant. Various changes in phenotype are of interest including modifying expression of a gene in a plant root, altering a plant's pathogen or insect defense mechanism, increasing the plants tolerance to herbicides in a plant, altering root development to respond to environmental stress, modulating the plant's response to salt, temperature (hot and cold), drought, and the like. These results can be achieved by the expression of a heterologous nucleotide sequence of interest comprising an appropriate gene product. In specific embodiments, the heterologous nucleotide sequence of interest is an endogenous plant sequence whose expression level is increased in the plant or plant part. Alternatively, the results can be achieved by providing for a reduction of expression of one or more endogenous gene products, particularly enzymes, transporters, or cofactors, or by affecting nutrient uptake in the plant. These changes result in a change in phenotype of the transformed plant.

General categories of nucleotide sequences of interest for the present invention include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, and environmental stress resistance (altered tolerance to cold, salt, drought, etc). It is recognized that any gene of interest can be operably linked to the promoter of the invention and expressed in the plant.

Insect resistance genes may encode resistance to pests that have great yield drag such as rootworm, cutworm, European corn borer, and the like. Such genes include, for example, *Bacillus thuringiensis* toxic protein genes (U.S. Pat. Nos. 5,366,892; 5,747,450; 5,736,514; 5,723,756; 5,593,881; and Geiser et al. (1986) *Gene* 48:109); and the like.

Genes encoding disease resistance traits include detoxification genes, such as those which detoxify fumonisin (U.S. Pat. No. 5,792,931); avirulence (avr) and disease resistance (R) genes (Jones et al. (1994) *Science* 266:789; Martin et al. (1993) *Science* 262:1432; and Mindrinos et al. (1994) *Cell* 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), glyphosate (e.g., the EPSPS gene and the GAT gene; see, for example, U.S. Publication No. 20040082770 and WO 03/092360) or other such genes known in the art. The bar gene encodes resistance to the herbicide basta, the nptll gene encodes resistance to the antibiotics kanamycin and geneticin, and the ALS gene mutants encode resistance to the herbicide chlorsulfuron.

Glyphosate resistance is imparted by mutant 5-enolpyruvl-3-phosphikimate synthase (EPSP) and aroA genes. See, for example, U.S. Pat. No. 4,940,835 to Shah et al., which discloses the nucleotide sequence of a form of EPSPS which can confer glyphosate resistance. U.S. Pat. No. 5,627,061 to Barry et al. also describes genes encoding EPSPS enzymes. See also U.S. Pat. Nos. 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and 5,491,288; and international publications WO 97/04103; WO 97/04114; WO 00/66746; WO 01/66704; WO 00/66747 and WO 00/66748, which are incorporated herein by reference for this purpose. Glyphosate resistance is also imparted to plants that express a gene that encodes a glyphosate oxido-reductase enzyme as described more fully in U.S. Pat. Nos. 5,776,760 and 5,463,175, which are incorporated herein by reference for this purpose. In addition glyphosate resistance can be imparted to plants by the over expression of genes encoding glyphosate N-acetyltransferase. See, for example, U.S. patent application Ser. Nos: 10/004,357; and 10/427,692.

Exogenous products include plant enzymes and products as well as those from other sources including prokaryotes and other eukaryotes. Such products include enzymes, cofactors, hormones, and the like.

Examples of other applicable genes and their associated phenotype include the gene which encodes viral coat protein and/or RNA, or other viral or plant genes that confer viral resistance; genes that confer fungal resistance; genes that promote yield improvement; and genes that provide for resistance to stress, such as cold, dehydration resulting from drought, heat and salinity, toxic metal or trace elements, or the like.

As noted, the heterologous nucleotide sequence operably linked to the MT1 promoters disclosed herein may be an antisense sequence for a targeted gene. Thus the promoter sequences disclosed herein may be operably linked to antisense DNA sequences to reduce or inhibit expression of a native protein in the plant root.

"RNAi" refers to a series of related techniques to reduce the expression of genes (See for example U.S. Pat. No. 6,506,559). Older techniques referred to by other names are now thought to rely on the same mechanism, but are given different names in the literature. These include "antisense inhibition," the production of antisense RNA transcripts capable of suppressing the expression of the target protein, and "co-suppression" or "sense-suppression," which refer to the production of sense RNA transcripts capable of suppressing the expression of identical or substantially similar foreign or endogenous genes (U.S. Pat. No. 5,231,020, incorporated herein by reference). Such techniques rely on the use of constructs resulting in the accumulation of double stranded RNA with one strand complementary to the target gene to be silenced. The MT2 promoters of the embodiments may be used to drive expression of constructs that will result in RNA interference including microRNAs and siRNAs.

The term "promoter" or "transcriptional initiation region" is intended to mean a regulatory region of DNA usually comprising a TATA box capable of directing RNA polymerase II to initiate RNA synthesis at the appropriate transcription initiation site for a particular coding sequence. A promoter may additionally comprise other recognition sequences generally positioned upstream or 5' to the TATA box, referred to as upstream promoter elements, which influence the transcription initiation rate. It is recognized that having identified the nucleotide sequences for the promoter regions disclosed herein, it is within the state of the art to isolate and identify further regulatory elements in the 5' untranslated region upstream from the particular promoter regions identified herein. Additionally, chimeric promoters may be provided. Such chimeras include portions of the promoter sequence fused to fragments and/or variants of heterologous transcriptional regulatory regions. Thus, the promoter regions disclosed herein can comprise upstream regulatory elements such as, those responsible for tissue and temporal expression of the coding sequence, enhancers and the like. In the same manner, the promoter elements, which enable expression in the desired tissue, such as the root, can be identified, isolated and used with other core promoters to confer root-preferred expression. In this aspect of the invention, a "core promoter" is intended to mean a promoter without promoter elements.

In the context of this disclosure, the term "regulatory element" also refers to a sequence of DNA, usually but not always, upstream (5') to the coding sequence of a structural gene, which includes sequences which control the expression of the coding region by providing the recognition for RNA polymerase and/or other factors required for transcription to start at a particular site. An example of a regulatory element that provides for the recognition for RNA polymerase or other transcriptional factors to ensure initiation at a particular site is a promoter element. A promoter element comprises a core promoter element, responsible for the initiation of transcription, as well as other regulatory elements (as discussed elsewhere in this application) that modify gene expression. It is to be understood that nucleotide sequences, located within introns, or 3' of the coding region sequence may also contribute to the regulation of expression of a coding region of interest. Examples of suitable introns include, but are not limited to, the maize IVS6 intron, or the maize actin intron. A regulatory element may also include those elements located downstream (3') to the site of transcription initiation, or within transcribed regions, or both. In the context of the present invention a post-transcriptional regulatory element may include elements that are active following transcription initiation, for example translational and transcriptional enhancers, translational and transcriptional repressors, and mRNA stability determinants.

The regulatory elements, or variants or fragments thereof, of the present invention may be operatively associated with heterologous regulatory elements or promoters in order to modulate the activity of the heterologous regulatory element. Such modulation includes enhancing or repressing transcriptional activity of the heterologous regulatory element, modulating post-transcriptional events, or either enhancing or repressing transcriptional activity of the heterologous regulatory element, and modulating post-transcriptional events. For example, one or more regulatory elements, or fragments thereof, of the present invention may be operatively associated with constitutive, inducible, or tissue-specific promoters or fragment thereof, to modulate the activity of such promoters within desired tissues in plant cells.

The regulatory sequences of the present invention, or variants or fragments thereof, when operably linked to a heterologous nucleotide sequence of interest can drive root-preferred expression of the heterologous nucleotide sequence in the root (or root part) of the plant expressing this construct. The term "root-preferred" is intended to mean that expression of the heterologous nucleotide sequence is most abundant in the root or a root part, including for example, the root cap, apical meristem, protoderm, ground meristem, procambium, endodermis, cortex, vascular cortex, epidermis, and the like. While some level of expression of the heterologous nucleotide sequence may occur in other plant tissue types, expression occurs most abundantly in the root or root part including primary, lateral and adventitious roots.

A "heterologous nucleotide sequence" is intended to mean a sequence that is not naturally occurring with the promoter sequence of the invention. While this nucleotide sequence is heterologous to the promoter sequence, it may be homologous, or native, or heterologous, or foreign, to the plant host.

The isolated promoter sequences of the present invention can be modified to provide for a range of expression levels of the heterologous nucleotide sequence. Thus, less than the entire promoter regions may be utilized and the ability to drive expression of the nucleic acid sequence of interest retained. It is recognized that expression levels of the mRNA may be altered in different ways by deletions of portions of the promoter sequences. The mRNA expression levels may be decreased, or alternatively, expression may be increased as a result of promoter deletions if, for example, there is a negative regulatory element (for a repressor) that is removed during the truncation process. Generally, at least about 20 nucleotides of an isolated promoter sequence will be used to drive expression of a nucleotide sequence.

It is recognized that to increase transcription levels, enhancers may be utilized in combination with the promoter regions of the invention. Enhancers are nucleotide sequences that act to increase the expression of a promoter region. Enhancers are known in the art and include the SV40 enhancer region, the 35S enhancer element, and the like. Some enhancers are also known to alter normal promoter expression patterns, for example, by causing a promoter to be expressed constitutively when without the enhancer, the same promoter is expressed only in one specific tissue or a few specific tissues.

Modifications of the isolated promoter sequences of the present invention can provide for a range of expression of the heterologous nucleotide sequence. Thus, they may be modified to be weak promoters or strong promoters. Generally, a "weak promoter" is intended to mean a promoter that drives expression of a coding sequence at a low level. A "low level" of expression is intended to mean expression at levels of about 1/10,000 transcripts to about 1/100,000 transcripts to about 1/500,000 transcripts. Conversely, a strong promoter drives expression of a coding sequence at a high level, or at about 1/10 transcripts to about 1/100 transcripts to about 1/1,000 transcripts.

It is recognized that the promoters of the invention may be used with their native MT coding sequences to increase or decrease expression, thereby resulting in a change in phenotype of the transformed plant. This phenotypic change could further affect an increase or decrease in levels of metal ions in tissues of the transformed plant.

The nucleotide sequences disclosed in the present invention, as well as variants and fragments thereof, are useful in the genetic manipulation of any plant. The MT1 promoter sequences are useful in this aspect when operably linked with a heterologous nucleotide sequence whose expression is to be controlled to achieve a desired phenotypic response. The term "operably linked" is intended to mean that the transcription or translation of the heterologous nucleotide sequence is under the influence of the promoter sequence. In this manner, the nucleotide sequences for the promoters of the invention may be provided in expression cassettes along with heterologous nucleotide sequences of interest for expression in the plant of interest, more particularly in the root of the plant.

Such expression cassettes will comprise a transcriptional initiation region comprising one of the promoter nucleotide sequences of the present invention, or variants or fragments thereof, operably linked to the heterologous nucleotide sequence. Such an expression cassette can be provided with a plurality of restriction sites for insertion of the nucleotide sequence to be under the transcriptional regulation of the regulatory regions. The expression cassette may additionally contain selectable marker genes as well as 3' termination regions.

The expression cassette can include, in the 5'–3' direction of transcription, a transcriptional initiation region (i.e., a promoter, or variant or fragment thereof, of the invention), a translational initiation region, a heterologous nucleotide sequence of interest, a translational termination region and, optionally, a transcriptional termination region functional in the host organism. The regulatory regions (i.e., promoters, transcriptional regulatory regions, and translational termination regions) and/or the polynucleotide of the embodiments may be native/analogous to the host cell or to each other. Alternatively, the regulatory regions and/or the polynucleotide of the embodiments may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

While it may be preferable to express a heterologous nucleotide sequence using the promoters of the invention, the native sequences may be expressed. Such constructs would change expression levels of the MT protein in the plant or plant cell. Thus, the phenotype of the plant or plant cell is altered.

The termination region may be native with the transcriptional initiation region, may be native with the operably linked DNA sequence of interest, may be native with the plant host, or may be derived from another source (i.e., foreign or heterologous to the promoter, the DNA sequence being expressed, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nucleic Acids Res.* 17:7891–7903; and Joshi et al. (1987) *Nucleic Acid Res.* 15:9627–9639.

The expression cassette comprising the sequences of the present invention may also contain at least one additional nucleotide sequence for a gene to be cotransformed into the organism. Alternatively, the additional sequence(s) can be provided on another expression cassette.

Where appropriate, the nucleotide sequences whose expression is to be under the control of the root-preferred promoter sequence of the present invention and any additional nucleotide sequence(s) may be optimized for increased expression in the transformed plant. That is, these nucleotide sequences can be synthesized using plant preferred codons for improved expression. See, for example, Campbell and Gowri (1990) *Plant Physiol.* 92:1–11 for a discussion of host-preferred codon usage. Methods are available in the art for synthesizing plant-preferred genes. See, for example, U.S. Pat. Nos. 5,380,831, 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the heterologous nucleotide sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Nat. Acad. Sci. USA* 86:6126–6130); potyvirus leaders, for example, TEV leader (Tobacco Etch Virus)

(Allison et al. (1986) *Virology* 154:9–20)); MDMV leader (Maize Dwarf Mosaic Virus); human immunoglobulin heavy-chain binding protein (BiP) (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) *Molecular Biology of RNA*, pages 237–256); and maize chlorotic mottle virus leader (MCMV) (Lommel et al. (1991) *Virology* 81:382–385). See also Della-Cioppa et al. (1987) *Plant Physiology* 84:965–968. Methods known to enhance mRNA stability can also be utilized, for example, introns, such as the maize Ubiquitin intron (Christensen and Quail (1996) *Transgenic Res.* 5:213–218; Christensen et al. (1992) *Plant Molecular Biology* 18:675–689) or the maize Adh1 intron (Kyozuka et al. (1991) *Mol. Gen. Genet.* 228:40–48; Kyozuka et al. (1990) *Maydica* 35:353–357), and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, for example, transitions and transversions, may be involved.

Reporter genes or selectable marker genes may be included in the expression cassettes. Examples of suitable reporter genes known in the art can be found in, for example, Jefferson et al. (1991) in *Plant Molecular Biology Manual*, ed. Gelvin et al. (Kluwer Academic Publishers), pp. 1–33; DeWet et al. (1987) *Mol. Cell. Biol.* 7:725–737; Goff et al. (1990) *EMBO J.* 9:2517–2522; Kain et al. (1995) *Bio Techniques* 19:650–655; and Chiu et al. (1996) *Current Biology* 6:325–330.

Selectable marker genes for selection of transformed cells or tissues can include genes that confer antibiotic resistance or resistance to herbicides. Examples of suitable selectable marker genes include, but are not limited to, genes encoding resistance to chloramphenicol (Herrera Estrella et al. (1983) *EMBO J.* 2:987–992); methotrexate (Herrera Estrella et al. (1983) *Nature* 303:209–213; Meijer et al. (1991) *Plant Mol. Biol.* 16:807–820); hygromycin (Waldron et al. (1985) *Plant Mol. Biol.* 5:103–108; Zhijian et al. (1995) *Plant Science* 108:219–227); streptomycin (Jones et al. (1987) *Mol. Gen. Genet.* 210:86–91); spectinomycin (Bretagne-Sagnard et al. (1996) *Transgenic Res.* 5:131–137); bleomycin (Hille et al. (1990) *Plant Mol. Biol.* 7:171–176); sulfonamide (Guerineau et al. (1990) *Plant Mol. Biol.* 15:127–136); bromoxynil (Stalker et al. (1988) *Science* 242:419–423); glyphosate (Shaw et al. (1986) *Science* 233:478–481); phosphinothricin (DeBlock et al. (1987) *EMBO J.* 6:2513–2518).

Other genes that could serve utility in the recovery of transgenic events but might not be required in the final product would include, but are not limited to, examples such as GUS (beta-glucuronidase; Jefferson (1987) *Plant Mol. Biol. Rep.* 5:387), GFP (green fluorescence protein; Chalfie et al. (1994) *Science* 263:802), luciferase (Riggs et al. (1987) *Nucleic Acids Res.* 15(19):8115 and Luehrsen et al. (1992) *Methods Enzymol.* 216:397–414) and the maize genes encoding for anthocyanin production (Ludwig et al. (1990) *Science* 247:449).

The expression cassette comprising the MT1 promoter of the present invention, operably linked to a nucleotide sequence of interest, can be used to transform any plant. In this manner, genetically modified plants, plant cells, plant tissue, seed, root, and the like can be obtained.

The methods of the invention involve introducing a nucleotide sequence into a plant. "Introducing" is intended to mean presenting to the plant the nucleotide sequence in such a manner that the sequence gains access to the interior of a cell of the plant. The methods of the invention do not depend on a particular method for introducing a sequence into a plant, only that the nucleotide sequence gains access to the interior of at least one cell of the plant. Methods for introducing nucleotide sequences into plants are known in the art including, but not limited to, stable transformation methods, transient transformation methods, and virus-mediated methods.

"Stable transformation" is intended to mean that the nucleotide construct introduced into a plant integrates into the genome of the plant and is capable of being inherited by the progeny thereof. "Transient transformation" is intended to mean that a nucleotide sequence is introduced into the plant and does not integrate into the genome of the plant or a polypeptide is introduced into a plant.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, *Agrobacterium*-mediated transformation (U.S. Pat. Nos. 5,563,055 and 5,981,840), direct gene transfer (Paszkowski et al. (1984) *EMBO J.* 3:2717–2722), and ballistic particle acceleration (see, for example, U.S. Pat. Nos. 4,945,050; 5,879,918; 5,886,244; 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923–926); and Lec1 transformation (WO 00/28058). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); U.S. Pat. Nos. 5,240,855; 5,322,783 and 5,324,646; Klein et al. (1988) *Plant Physiol.* 91:440–444 (maize); Fromm et al. (1990) *Biotechnology* 8:833–839 (maize); Hooykaas-Van Slogteren et al. (1984) *Nature* (London) 311:763–764; U.S. Pat. No. 5,736,369 (cereals); Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, New York), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

In specific embodiments, the DNA constructs comprising the promoter sequences of the invention can be provided to a plant using a variety of transient transformation methods. Such transient transformation methods include, but are not limited to, viral vector systems and the precipitation of the polynucleotide in a manner that precludes subsequent release of the DNA. Thus, the transcription from the particle-bound DNA can occur, but the frequency with which its released to become integrated into the genome is greatly reduced. Such methods include the use particles coated with polyethylimine (PEI; Sigma #P3143).

In other embodiments, the polynucleotide of the invention may be introduced into plants by contacting plants with a virus or viral nucleic acids. Generally, such methods involve incorporating a nucleotide construct of the invention within a viral DNA or RNA molecule. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209–221; herein incorporated by reference.

Methods are known in the art for the targeted insertion of a nucleotide sequence at a specific location in the plant genome. In one embodiment, the insertion of the DNA construct comprising the heterologous nucleotide sequence of interest at a desired genomic location is achieved using a site-specific recombination system. See, for example, WO99/25821, WO99/25854, WO99/25840, WO99/25855, and WO99/25853, all of which are herein incorporated by reference. Briefly, the promoter of the invention can be contained in transfer cassette flanked by two non-recombinogenic recombination sites. The transfer cassette is introduced into a plant have stably incorporated into its genome a target site which is flanked by two non-recombinogenic recombination sites that correspond to the sites of the transfer cassette. An appropriate recombinase is provided and the transfer cassette is integrated at the target site. The DNA construct comprising the heterologous nucleotide sequence of interest is thereby integrated at a specific chromosomal position in the plant genome.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into its genome.

The article "a" and "an" are used herein to refer to one or more than one (i.e., to at least one) of the grammatical object of the article. By way of example, "an element" means one or more element.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

The following examples are offered by way of illustration and not by way of limitation.

EXPERIMENTAL

EXAMPLE 1

Amplification and Reconstruction of the 1.8 kb Metallothionein (MT 1) Promoter

The 1.8 kb promoter sequence upstream of the root metallothionein (MT1) gene was obtained by genome walking using the GenomeWalker™ kit (BD Biosciences Clontech, Palo Alto, Calif.) following the manufacturer's protocol. The sequence of the 1.8 kb MT1 promoter was generated by performing three genome walking steps upstream of a smaller 747 base pair (bp) MT promoter (SEQ ID NO:2). Two nested gene specific primers were designed utilizing SEQ ID NO. 2 as a template. In the first step, two nested gene specific primers named rootmet5 (SEQ ID NO:3) and rootmet7 (SEQ ID NO:4) were used to amplify via the polymerase chain reaction (PCR) a 683 bp fragment that was cloned into the pCR®2.1-TOPO® vector (Invitrogen, Carlsbad, Calif.). This clone was named pTOPO®-RM22.

In the second step, two different nested gene specific primers designed from pTOPO-RM22 sequence, named rootmet1 (SEQ ID NO:5) and rootmet2 (SEQ ID NO:6) were used to PCR amplify a 300 bp fragment. This PCR product was cloned into the pCR®2.1-TOPO® vector to generate a clone named pTOPO®-Rootmet12. The insert in pTOPO®-Rootmet12 was then sequenced.

In the final step, a third set of nested primers named rootmet3KRW3 (SEQ ID NO:7) and rootmet3KRW4 (SEQ ID NO:8) was used to perform an additional genome walking step upstream of the pTOPO®-Rootmet12 insert sequence. This final step generated an 871 bp PCR product which was cloned into pCR®2.1-TOPO® and then sequenced. This final clone was named pTOPO®-FRAG53.

For each genome walking step, the following PCR conditions were used: 94° C. for 1 min. followed by 20 cycles of: 94° C. for 15 sec. and 65° C. for 4 min. (reduced by 0.5° C. per cycle) and 15 cycles of: 94° C. for 15 sec. and 55° C. for 4 min.

The full length MT1 promoter was then assembled from a subset of the cloned genome walker fragments using splicing by overlap extension (SOE) as described below. pTOPO®-Rootmet12 was not used in the SOE process since the SOE primers that were designed to bridge the sequence from pTOPO®-RM22 and pTOPO®-FRAG53 included the region of pTOPO®-Rootmet12 not present in either of the above clones. SOE was performed due to the difficulties encountered during PCR amplification of the 1.8 kb promoter fragment directly from maize genomic DNA.

SOE—Round 1

In the first step of SOE, round 1, PCR primers were used to amplify promoter fragments individually utilizing pTOPO®-RM22 and pTOPO®-FRAG53 as templates. An 894 bp promoter fragment was PCR amplified from pTOPO®-FRAG53 using primers named RMSOE1 (SEQ ID NO:9) and RMSOE4 (SEQ ID NO:10). A BamHI site was added to the 5' end of RMSOE1 to facilitate subcloning of the full promoter fragment.

A 672 bp promoter fragment was PCR amplified from pTOPO®-RM22 using primers named RMSOE3 (SEQ ID NO:11) and RMSOE2 (SEQ ID NO:12). RMSOE3 and RMSOE4 were designed such that the 36 nucleotides at the 3' end of each primer were complementary to each other in order to facilitate the annealing of the two separate PCR products in the second step of SOE.

The PCR conditions for the first step of SOE, round 1, were as follows: 94° C. for 30 sec. followed by 30 cycles of: 94° C. for 30 sec., 42° C. for 1 min., and 72° C. for 30 sec. followed by 72° C. for 5 min.

The PCR products were gel purified and used as templates for the second step of SOE. In the second step of SOE the purified 894 and 672 bp PCR products from step 1 were used as templates for PCR with the primers named RMSOE1 (SEQ ID NO:9) and RMSOE2 (SEQ ID NO:12).

The PCR conditions for the second step of SOE, round 1, were as follows: 94° C. for 5 min. followed by 30 cycles of: 94° C. for 30 sec., 50° C. for 1 min., and 72° C. for 30 sec., followed by 72° C. for 7 min.

The resulting 1.52 kb fragment was cloned into pCR®2.1-TOPO® and sequence confirmed. This clone was named pTOPO®-SOE1.

SOE—Round 2

A further round of SOE, round 2, was performed to add the remainder of the sequence for the 1.8 kb MT1 promoter. In the first step two primers named BAMrootmetpro8 (SEQ ID NO:13) and pSOEB (SEQ ID NO:14) were used to PCR amplify a 1.2 kb promoter fragment from the clone named pTOPO®-SOE1. Then, primers named pSOEA (SEQ ID NO:15) and Xhorootmet1b (SEQ ID NO:16) were used to PCR amplify a 656 bp product from a plasmid containing the original 747 bp MT promoter (SEQ ID NO:2). An XhoI site was incorporated into the Xhorootmet1b primer to facilitate future subcloning. pSOEA and pSOEB contained 20 nucleotides of complementary sequence at their 5' ends so that the two PCR products in the second step of SOE would readily anneal.

Each PCR reaction for the first step of round 2 used the following conditions: 94° C. for 5 min. followed by 30 cycles of: 94° C. for 30 sec., 50° C. for 1 min., and 72° C. for 30 sec., followed by 72° C. for 7 min.

The 1.2 kb and 0.66 kb PCR products from step one of round 2 were gel purified and used as templates for the second step (round 2) of SOE. The primers used in the second step were BAMrootmetpro8 (SEQ ID NO:13) and Xhorootmet1b (SEQ ID NO:16).

The PCR conditions for the second step of SOE, round 2, were as follows: 94° C. for 30 sec. followed by 30 cycles of: 94° C. for 30 sec., 50° C. for 1 min., and 72° C. for 30 sec., followed by 72° C. for 5 min.

The resulting 1.8 kb PCR fragment (i.e., the 1.8 kb MT1 promoter) was cloned into pCR®2.1-TOPO® and sequence confirmed. This clone was named RM2-2.

EXAMPLE 2

Transformation and Regeneration of Transgenic Plants

Immature maize embryos from greenhouse donor plants are bombarded with a plasmid containing a gene of interest operably linked to an MT1 promoter of the invention, plus a plasmid containing the selectable marker gene PAT (Wohlleben et al. (1988) *Gene* 70:25–37) that confers resistance to the herbicide Bialaphos. Transformation is performed as follows. Media recipes follow below.

To prepare target tissue, the ears are surface sterilized in 30% Chlorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5 cm target zone in preparation for bombardment.

To prepare DNA, a plasmid vector comprising a gene of interest operably linked to an MT1 promoter of the invention is made. This plasmid DNA plus plasmid DNA containing a PAT selectable marker is precipitated onto 1.1 μm (average diameter) tungsten pellets using a $CaCl_2$ precipitation procedure as follows: 100 μL prepared tungsten particles in water; 10 μL (1 μg) DNA in TrisEDTA buffer (1 μg total); and, 100 μL 2.5 M $CaCl_2$; 10 μL 0.1 M spermidine.

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 mL 100% ethanol, and centrifuged for 30 seconds. Again the liquid is removed, and 105 μL 100% ethanol is added to the final tungsten particle pellet. For particle gun bombardment, the tungsten/DNA particles are briefly sonicated and 10 μL spotted onto the center of each macrocarrier and allowed to dry about 2 minutes before bombardment.

The sample plates are bombarded at level #4 in particle gun #HE34-1 or #HE34-2. All samples receive a single shot at 650 PSI, with a total of ten aliquots taken from each tube of prepared particles/DNA.

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for root-preferred activity of the gene of interest or for altered metal ion levels.

The bombardment and culture media employed is as follows. Bombardment medium (560Y) comprises 4.0 g/L N6 basal salts (SIGMA C-1416), 1.0 mL/L Eriksson's Vitamin Mix (1000×SIGMA-1511), 0.5 mg/L thiamine HCl, 120.0 g/L sucrose, 1.0 mg/L 2,4-D, and 2.88 g/L L-proline (brought to volume with D-I $H_2O$ following adjustment to pH 5.8 with KOH); 2.0 g/L Gelrite (added after bringing to volume with D-I $H_2O$); and 8.5 mg/L silver nitrate (added after sterilizing the medium and cooling to room temperature). Selection medium (560R) comprises 4.0 g/L N6 basal salts (SIGMA C-1416), 1.0 mL/L Eriksson's Vitamin Mix (1000×SIGMA-1511), 0.5 mg/L thiamine HCl, 30.0 g/L sucrose, and 2.0 mg/L 2,4-D (brought to volume with D-I $H_2O$ following adjustment to pH 5.8 with KOH); 3.0 g/L Gelrite (added after bringing to volume with D-I $H_2O$); and 0.85 mg/L silver nitrate and 3.0 mg/L bialaphos(both added after sterilizing the medium and cooling to room temperature).

Plant regeneration medium (288J) comprises 4.3 g/L MS salts (GIBCO 11117-074), 5.0 mL/L MS vitamins stock solution (0.100 g nicotinic acid, 0.02 g/L thiamine HCl, 0.10 g/L pyridoxine HCl, and 0.40 g/L glycine brought to volume with polished D-I $H_2O$) (Murashige and Skoog (1962) *Physiol. Plant.* 15:473), 100 mg/L myo-inositol, 0.5 mg/L zeatin, 60 g/L sucrose, and 1.0 mL/L of 0.1 mM abscisic acid (brought to volume with polished D-I $H_2O$ after adjusting to pH 5.6); 3.0 g/L Gelrite (added after bringing to volume with D-I $H_2O$); and 1.0 mg/L indoleacetic acid and 3.0 mg/L bialaphos (added after sterilizing the medium and cooling to 60° C.). Hormone-free medium (272V) comprises 4.3 g/L MS salts (GIBCO 11117-074), 5.0 mL/L MS vitamins stock solution (0.100 g/L nicotinic acid, 0.02 g/L thiamine HCl, 0.10 g/L pyridoxine HCl, and 0.40 g/L glycine brought to volume with polished D-I $H_2O$), 0.1 g/L myo-inositol, and 40.0 g/L sucrose (brought to volume with polished D-I $H_2O$ after adjusting pH to 5.6); and 6 g/L bacto-agar (added after bringing to volume with polished D-I $H_2O$), sterilized and cooled to 60° C.

EXAMPLE 3

Expression Data Using the Promoter Sequences of the Invention

B73 seeds were placed along one edge of growth paper soaked in a solution of 7% sucrose. An additional piece of growth paper identical in size to the first was also soaked in 7% sucrose and overlaid onto the seeds. The growth paper-seed -growth paper sandwich was subsequently jelly rolled with the seed edge at the top of the roll. The roll was directionally placed into a beaker of 7% sucrose solution with the seeds at the top to allow for straight root growth. Seeds were allowed to germinate and develop for 2–3 days in the dark at 27–28° C. Prior to bombardment the outer skin layer of the cotyledon was removed and seedlings were placed in a sterile petri dish (60 mm) on a layer of Whatman #1 filter paper moistened with 1 mL of $H_2O$. Two seedlings per plate were arranged in opposite orientations and anchored to the filter paper with a 0.5% agarose solution. 2–3 cm root tip sections were also excised from seedlings and arranged lengthwise in the plates for bombardment.

DNA/gold particle mixtures were prepared for bombardment in the following method. Sixty mg of 0.6–1.0 micron gold particles were pre-washed with ethanol, rinsed with sterile distilled $H_2O$, and resuspended in a total of 1 mL of sterile $H_2O$. 50 μL aliquots of gold particle suspension were stored in siliconized Eppendorf tubes at room temperature. DNA was precipitated onto the surface of the gold particles by combining, in order, 50 μL aliquot of pre-washed 0.6 μM gold particles, 5–10 μg of test DNA, 50 μL 2.5 M $CaCl_2$ and 25 μL of 0.1 M spermidine. The solution was immediately vortexed for 3 minutes and centrifuged briefly to pellet the DNA/gold particles. The DNA/gold was washed once with 500 μL of 100% ethanol and suspended in a final volume of 50 μL of 100% ethanol. The DNA/gold solution was incubated at −20° C. for at least 60 minutes prior to aliquoting 6 μL of the DNA/gold mixture onto each Mylar™ macrocarrier.

Seedlings prepared as indicated above and excised root tips were bombarded twice using the PDS-1000/He gun at 1100 psi under 27–28 inches of Hg vacuum. The distance between macrocarrier and stopping screen was between 6–8 cm. Plates were incubated in sealed containers for 24 hours in the dark at 27–28° C. following bombardment.

After 18–24 hours of incubation the bombarded seedlings and root tips were assayed for transient GUS expression. Seedlings and excised roots were immersed in 10–15 mL of assay buffer containing 100 mM $NaH_2PO_4$—$H_2O$ (pH 7.0), 10 mM EDTA, 0.5 mM $K_4Fe(CN)_6$—$3H_2O$, 0.1% Triton X-100 and 2 mM 5-bromo-4-chloro-3-indoyl glucuronide. The tissues were incubated in the dark for 24 h at 37° C. Replacing the GUS staining solution with 100% ethanol stopped the assay. GUS expression/staining was visualized under a microscope.

Table 1 shows transient bombardment results for the 1.8 kb root met promoter:GUS construct, as well as a control ubiquitin promoter:GUS construct, in leaf, excised root, and seedling tissue. GUS expression driven by the root met promoter was observed in roots and seedlings but not leaf tissue. GUS expression driven by the ubiquitin control construct was observed in all tissues.

TABLE 1

Rootmet1 Promoter Expression in Bombarded Tissues

| Tissue | Rootmet promoter:GUS construct expression | Ubiquitin promoter:GUS construct expression |
|---|---|---|
| leaf | − | ++++ |
| root | +++ | ++++ |
| seedling | +++ | ++++ |

Scoring:
− no expression
+ weak expression levels compared to Ubi:GUS control
++ medium expression levels compared to Ubi:GUS control
+++ strong expression levels compared to Ubi:GUS control
++++ very strong expression levels compared to Ubi:GUS control

EXAMPLE 4

Transformation and Regeneration of Transgenic Plants using *Agrobacterium* Mediated Transformation For *Agrobacterium*-mediated transformation of maize with an MT1 promoter sequence of the embodiments, the method of Zhao was employed (U.S. Pat. No. 5,981,840, (hereinafter the '840 patent) and PCT patent publication WO98/32326; the contents of which are hereby incorporated by reference).

*Agrobacterium* were grown on a master plate of 800 medium and cultured at 28° C. in the dark for 3 days, and thereafter stored at 4° C. for up to one month. Working plates of *Agrobacterium* were grown on 810 medium plates and incubated in the dark at 28° C. for one to two days.

Briefly, embryos were dissected from fresh, sterilized corn ears and kept in 561Q medium until all required embryos were collected. Embryos were then contacted with an *Agrobacterium* suspension prepared from the working plate, in which the *Agrobacterium* contained a plasmid comprising the promoter sequence of the embodiments. The embryos were co-cultivated with the *Agrobacterium* on 562P plates, with the embryos placed axis down on the plates, as per the '840 patent protocol.

After one week on 562P medium, the embryos were transferred to 563O medium. The embryos were subcultured on fresh 563O medium at 2 week intervals and incubation was continued under the same conditions. Callus events began to appear after 6 to 8 weeks on selection.

After the calli had reached the appropriate size, the calli were cultured on regeneration (288W) medium and kept in the dark for 2–3 weeks to initiate plant regeneration. Following somatic embryo maturation, well-developed somatic embryos were transferred to medium for germination (272V) and transferred to a lighted culture room. Approximately 7–10 days later, developing plantlets were transferred to 272V hormone-free medium in tubes for 7–10 days until plantlets were well established. Plants were then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity.

Media Used in *Agrobacterium*-Mediated Transformation and Regeneration of Transgenic Maize Plants:

561Q medium comprises 4.0 g/L N6 basal salts (SIGMA C-1416), 1.0 mL/L Eriksson's Vitamin Mix (1000×SIGMA-1511), 0.5 mg/L thiamine HCl, 68.5 g/L sucrose, 36.0 g/L glucose, 1.5 mg/L 2,4-D, and 0.69 g/L L-proline (brought to volume with dl $H_2O$ following adjustment to pH 5.2 with KOH); 2.0 g/L Gelrite™ (added after bringing to volume with dl $H_2O$); and 8.5 mg/L silver nitrate (added after sterilizing the medium and cooling to room temperature).

800 medium comprises 50.0 mL/L stock solution A and 850 mL dl $H_2O$, and brought to volume minus 100 mL/L with dl $H_2O$, after which is added 9.0 g of phytagar. After sterilizing and cooling, 50.0 mL/L stock solution B is added, along with 5.0 g of glucose and 2.0 mL of a 50 mg/mL stock solution of spectinomycin. Stock solution A comprises 60.0 g of dibasic $K_2HPO_4$ and 20.0 g of monobasic sodium phosphate, dissolved in 950 mL of water, adjusted to pH 7.0 with KOH, and brought to 1.0 L volume with dl $H_2O$. Stock solution B comprises 20.0 g $NH_4Cl$, 6.0 g $MgSO_4.7H_2O$, 3.0 g potassium chloride, 0.2 g $CaCl_2$, and 0.05 g of $FeSO_4.7H_2O$, all brought to volume with dl $H_2O$, sterilized, and cooled.

810 medium comprises 5.0 g yeast extract (Difco), 10.0 g peptone (Difco), 5.0 g NaCl, dissolved in dl $H_2O$, and brought to volume after adjusting pH to 6.8. 15.0 g of bacto-agar is then added, the solution is sterilized and cooled, and 1.0 mL of a 50 mg/mL stock solution of spectinomycin is added.

562P medium comprises 4.0 g/L N6 basal salts (SIGMA C-1416), 1.0 mL/L Eriksson's Vitamin Mix (1000×SIGMA-1511), 0.5 mg/L thiamine HCl, 30.0 g/L sucrose, and 2.0 mg/L 2,4-D (brought to volume with dl $H_2O$ following adjustment to pH 5.8 with KOH); 3.0 g/L Gelrite™ (added after bringing to volume with dl $H_2O$); and 0.85 mg/L silver nitrate and 1.0 mL of a 100 mM stock of acetosyringone (both added after sterilizing the medium and cooling to room temperature).

563O medium comprises 4.0 g/L N6 basal salts (SIGMA C-1416), 1.0 mL/L Eriksson's Vitamin Mix (1000×SIGMA-1511), 0.5 mg/L thiamine HCl, 30.0 g/L sucrose, 1.5 mg/L 2,4-D, 0.69 g L-proline, and 0.5 g MES buffer (brought to volume with dl $H_2O$ following adjustment to pH 5.8 with KOH). Then, 6.0 g/L Ultrapure™ agar-agar (EM Science) is added and the medium is sterilized and cooled. Subsequently, 0.85 mg/L silver nitrate, 3.0 mL of a 1 mg/mL stock of Bialaphos, and 2.0 mL of a 50 mg/mL stock of carbenicillin are added.

288 W comprises 4.3 g/L MS salts (GIBCO 11117-074), 5.0 mL/L MS vitamins stock solution (0.100 g nicotinic acid, 0.02 g/L thiamine HCl, 0.10 g/L pyridoxine HCl, and 0.40 g/L Glycine brought to volume with polished D-I $H_2O$) (Murashige and Skoog (1962) *Physiol. Plant.* 15:473), 100 mg/L myo-inositol, 0.5 mg/L zeatin, and 60 g/L sucrose, which is then brought to volume with polished D-I $H_2O$ after adjusting to pH 5.6. Following, 6.0 g/L of Ultrapure™ agar—agar (EM Science) is added and the medium is sterilized and cooled. Subsequently, 1.0 mL/L of 0.1 mM abscisic acid; 1.0 mg/L indoleacetic acid and 3.0 mg/L Bialaphos are added, along with 2.0 mL of a 50 mg/mL stock of carbenicillin.

A recipe for 272V is provided in Example 3.

EXAMPLE 5

Expression Pattern of MT1 in Transgenic Plants

Stable transformed plants were created using *Agrobacterium* transformation protocols as per Example 4, to allow for a more detailed characterization of promoter activity.

To begin, leaf and root tissue from regenerated plants growing on nutrient agar stably transformed with an expression cassette containing the 1815 bp MT1 promoter (SEQ ID NO:1) operably connected to the GUS gene (abbreviated as MT1:GUS) was sampled to test for the presence of GUS activity. Histochemical analysis showed GUS was expressed in approximately 95% of the events generated (21 out of 22 events). In the group of expressing plants, approximately ⅓ or 7 plants had expression only in roots. The remaining ⅔ or 14 plants had expression in both leaves and roots.

To further characterize the MT1 promoter, 17 transgenic plants were forwarded to the greenhouse where they were evaluated under normal growing conditions. Four of the 17 plants sent had expression in roots only. The other 13 plants had both leaf and root expression. Leaf and root tissue were sampled from 16 plants (one plant died reducing the total number of plants in the greenhouse to 16) at the developmental stage, V5 (5 collared leaves). All 16 plants had GUS expression in nodal roots, as determined by histochemical staining. Fifteen of these plants were rated as having a level of staining that was comparable to ubi:GUS expressing plants. Identical results were obtained for lateral roots. The ubiquitin promoter is considered to be a strong promoter (Christensen et al. (1989) *Plant Mol. Biol.* 12:619–632 and Christensen et al. (1992) *Plant Mol. Biol.* 18:675–689) and ubi:GUS expressing plants were generated as a positive control for the evaluation of the MT1 events.

GUS expression was observed in leaves. Abaxial sections of the V5 leaf were histochemically stained and 15 of the 16 plants had observable GUS staining. Nine of the 15 plants had a level of staining comparable to the level of staining in the leaves of ubi:GUS plants. Interestingly, of the 4 plants that had only root expression while growing on nutrient agar, 3 now had GUS expression in the leaves. GUS expression was also detected in tassels. Fourteen out of 14 plants stained for GUS. Silks, on the other hand, did not have much GUS expression and only 3 of 13 plants had expression in silks. No staining was observed in pollen from any of the plants.

Beside the lack of expression in pollen, the staining observed, particularly in the leaves and tassels, does not correlate well with the MPSS data for the rootmet1 gene, which indicated expression of the gene was root-preferred. MPSS or Massively Parallel Signature Sequencing (see Brenner S, et al. (2000) *Nature Biotechnology* 18:630–634, Brenner S et al. (2000) *Proc Natl Acad Sci USA* 97:1665–1670) is a method that can be used to determine the expression pattern of a particular native gene and its expression level in different tissues. The inconsistency between the native expression pattern and the expression pattern in the transgenic plants might be due to the presence of the 35S enhancer in the test vector. The enhancer altered the expression pattern of a related promoter, MT2 (U.S. Provisional Application No 60/531,793 filed Dec. 22, 2003, herein incorporated by reference). Alternatively, it is possible that elements necessary for root-preferred expression are not present in the MT1 promoter fragment. However, the transient bombardment results in Example 3 showed root-preferred expression.

Regardless, the expression data show that the MT1 promoter is a functional genetic element. It is capable of directing transgene expression in maize plants and could be useful in cases where low or no expression in pollen and silks is desired. The MT1 promoter would also be particularly useful in cases when expression in pollen is specifically not desired.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

What is claimed is:

1. An isolated nucleic acid molecule comprising a nucleotide sequence selected from the group consisting of:
   a) a nucleotide sequence comprising the sequence set forth in SEQ ID NO: 1;
   b) a nucleotide sequence comprising the full-length metallothionein 1 promoter sequence of the plasmid deposited as Patent Deposit No. NRRL B-30792; and,
   c) a nucleotide sequence comprising at least 1000 contiguous nucleotides of the sequence set forth in SEQ ID NO: 1, wherein said nucleotide sequence comprising at least 1000 contiguous nucleotides of the sequence set forth in SEQ ID NO: 1 initiates transcription in a plant cell.

2. An expression cassette comprising the nucleotide sequence of claim 1 operably linked to a heterologous nucleotide sequence of interest.

3. A vector comprising the expression cassette of claim 2.

4. A plant cell comprising the expression cassette of claim 2.

5. The plant cell of claim 4, wherein said expression cassette is stably incorporated into the genome of the plant cell.

6. The plant cell of claim 4, wherein said plant cell is from a monocot.

7. The plant cell of claim 6, wherein said monocot is maize.

8. The plant cell of claim 4, wherein said plant cell is from a dicot.

9. A plant comprising the expression cassette of claim 2.

10. The plant of claim 9, wherein said plant is a monocot.

11. The plant of claim 10, wherein said monocot is maize.

12. The plant of claim 9, wherein said plant is a dicot.

13. The plant of claim 9, wherein said expression cassette is stably incorporated into the genome of the plant.

14. A transgenic seed of the plant of claim 13, wherein the seed comprises the expression cassette.

15. The plant of claim 9, wherein the heterologous nucleotide sequence of interest encodes a gene product tat confers herbicide, salt, cold, drought, pathogen, or insect resistance.

16. A method for expressing a nucleotide sequence in a plant or a plant cell, said method comprising introducing into the plant or the plant cell an expression cassette comprising a promoter operably linked to a heterologous nucleotide sequence of interest, wherein said promoter comprises a nucleotide sequence selected from the group consisting of:
   a) a nucleotide sequence comprising the sequence set forth in SEQ ID NO: 1;
   b) a nucleotide sequence comprising the full-length metallothionein 1 promoter sequence of the plasmid deposited as Patent Deposit No. NRRL B-30792; and,
   c) a nucleotide sequence comprising at least 1000 contiguous nucleotides of the sequence set forth in SEQ ID NO: 1, wherein said nucleotide sequence comprising at least 1000 contiguous nucleotides of the sequence set forth in SEQ ID NO: 1 initiates transcription in a plant cell.

17. The method of claim 16, wherein the heterologous nucleotide sequence of interest encodes a gene product that confers herbicide, salt, cold, drought, pathogen, or insect resistance.

18. The method of claim 16, wherein said heterologous nucleotide sequence of interest is expressed in a root-preferred manner.

19. A method for expressing a nucleotide sequence in a root-preferred manner in a plant, said method comprising introducing into a plant cell an expression cassette and regenerating a plant from said cell, said plant having stably incorporated into its genome the expression cassette, said expression cassette comprising a promoter operably linked to a heterologous nucleotide sequence of interest, wherein said promoter comprises a nucleotide sequence selected from the group consisting of:
   a) a nucleotide sequence comprising the sequence set forth in SEQ ID NO: 1;
   b) a nucleotide sequence comprising the full-length metallothionein 1 promoter sequence of the plasmid deposited as Patent Deposit No. NRRL B-30792; and,
   c) a nucleotide sequence comprising at least 1000 contiguous nucleotides of the sequence set forth in SEQ ID NO: 1, wherein said nucleotide sequence comprising at least 1000 contiguous nucleotides of the sequence set forth in SEQ ID NO: 1 initiates transcription in a plant root cell.

20. The method of claim 19, wherein expression of said heterologous nucleotide sequence of interest alters the phenotype of said plant.

\* \* \* \* \*

UNITED STATES PATENT AND TRADEMARK OFFICE
CERTIFICATE OF CORRECTION

| | | |
|---|---|---|
| PATENT NO. | : 7,214,854 B2 | Page 1 of 1 |
| APPLICATION NO. | : 11/022111 | |
| DATED | : May 8, 2007 | |
| INVENTOR(S) | : Diehn et al. | |

It is certified that error appears in the above-identified patent and that said Letters Patent is hereby corrected as shown below:

Item (56) References Cited,
U.S. PATENT DOCUMENTS: "2002/0132139 A1" should read --2002/0162139 A1--

Column 35, Claim 15,
Line 16: "tat" should read --that--

Signed and Sealed this

Fourteenth Day of August, 2007

JON W. DUDAS
*Director of the United States Patent and Trademark Office*